United States Patent
Matthiessen et al.

(10) Patent No.: US 7,807,435 B2
(45) Date of Patent: Oct. 5, 2010

(54) METHOD FOR THE PURIFICATION OF ALPHA-1 PROTEINASE INHIBITOR (A1PI)

(75) Inventors: Peter Matthiessen, Vienna (AT); Gerald Brachtl, Vienna (AT); Peter Turecek, Klosterneuburg (AT); Hans-Peter Schwarz, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 11/202,349

(22) Filed: Aug. 11, 2005

(65) Prior Publication Data

US 2007/0037270 A1 Feb. 15, 2007

(51) Int. Cl.
C12N 9/99 (2006.01)
(52) U.S. Cl. ........................................ 435/219; 435/184
(58) Field of Classification Search .................. None
See application file for complete search history.

(56) References Cited

U.S. PATENT DOCUMENTS

| 4,629,567 A | | 12/1986 | Bollen et al. | |
|---|---|---|---|---|
| 5,891,843 A | * | 4/1999 | Turecek et al. | 514/2 |
| 6,093,804 A | * | 7/2000 | Ralston et al. | 530/416 |

FOREIGN PATENT DOCUMENTS

| WO | 95/35306 | 12/1995 |
|---|---|---|
| WO | 98/00154 | 1/1998 |

OTHER PUBLICATIONS

Advanced Minerals Corporation 2003, http: // www. advancedminerals.com/celpure.htm , pp. 1-3.*
Soejima et al., "A Novel Human Metalloprotease Synthesized in the Liver and Secreted into the Blood: Possibly, the von Willebrand Factor-Cleaving Protease?", Journal of Biochemistry, 2001, vol. 130, pp. 475-480.*
Cohn et al.; "Preparation and Properties of Serum and Plasma Proteins"; *J Am Chem Soc*; vol. 68; pp. 459-475 (1946).
Hein et al. ; "Production of Alpha$_1$-Proteinase Inhibitor (Human)" ; *Eur Respir J* ; vol. 3 :9 ; pp. 16s-20s (1990).
Huang et al. ; "Expression and Purification of Functional Human $\alpha$-1-Antitrypsin from Cultured Plant Cells" ; *Biotechnol Prog* ; vol. 17; pp. 126-133 (2001).
Kwon et al. ; "Purification and Characterization of $\alpha_1$-Antitrypsin Secreted by Recombinant Yeast *Saccharomyces diastaticus*"; *J of Biotechnol*; vol. 42; pp. 191-195 (1995).
Mahadeva et al.; "Alpha$_1$-Antitrypsin Deficiency, Cirrhosis and Emphysema"; *Thorax*; vol. 53; pp. 501-505 (1998).
Mattes et al.; "Preparation and Properties of an Alpha-1-Protease Inhibitor Concentrate with High Specific Activity"; *Vox Sang*; vol. 81:1; pp. 29-36 (2001).
Wright et al.; "High Level Expression of Active Human Alpha-1-Antitrypsin in the Milk of Transgenic Sheep"; *Bio/Technology*; vol. 9:9; pp. 830-834 (1991).
Advanced Minerals Corporation; Technical Note AMC02, Version 3.5; "Comparing Conventional Diatomite and Celpure® Filter Aids"; 2 pages (2002).
Aldrich® Brochure; "Celpure® P Clarification Media"; 2 pages.
The Alpha-1-Antitrypsin Deficiency Registry Study Group (Crystal et al.); "Survival and FEV$_1$ Decline in Individuals with Severe Deficiency of $\alpha_1$-Antitrypsin"; *Am J Respir Crit Care Med*; vol. 158; pp. 49-59 (1998).
Archibald et al.; "High-Level Expression of Biologically Active Human $\alpha_1$-Antitrypsin in the Milk of Transgenic Mice"; *Proc Natl Acad Sci USA*; vol. 87; pp. 5178-5182 (1990).
Bischoff et al.; "Purification and Biochemical Characterization of Recombinant $\alpha_1$-Antitrypsin Variants Expressed in *Escherichia coil*"; *Biochemistry*; vol. 30:14; pp. 3464-3472 (1991).
Coan et al.; "Preparation and Properties of Alpha$_1$-Proteinase Inhibitor Concentrate from Human Plasma"; *Vox Sang*; vol. 48; pp. 333-342 (1985).

* cited by examiner

*Primary Examiner*—Jon P Weber
*Assistant Examiner*—Laura Schuberg
(74) *Attorney, Agent, or Firm*—Townsend and Townsend and Crew LLP

(57) ABSTRACT

The present invention relates to a method for the purification of alpha-1 proteinase inhibitor (a1PI) from protein fractions. More specifically, the invention relates to an improved method for the purification of alpha-1 proteinase inhibitor (a1PI), wherein the yield of a1PI can be increased by thawing the starting material and incubating it for several hours before subjecting it to a washing step.

14 Claims, 10 Drawing Sheets

METHOD FOR THE PURIFICATION OF ALPHA-1 PROTEINASE INHIBITOR (A1PI)

FIELD OF THE INVENTION

The present invention relates to a method for the purification of alpha-1 proteinase inhibitor (a1PI) from protein fractions. More specifically, the invention relates to an improved method for the purification of alpha-1 proteinase inhibitor (a1PI), wherein the yield of a1PI can be increased by thawing the starting material and incubating it for several hours before subjecting it to a washing step.

BACKGROUND OF THE INVENTION

Alpha-1 proteinase inhibitor (a1PI), also named alpha-1-antitrypsin (AAT), is a glycopeptide inhibitor of proteases, and is found in human serum and other fluids. Protease inhibition by a1PI is an essential component of the regulation of tissue proteolysis, and a1PI deficiency is implicated in the pathology of several diseases. Individuals who inherit an a1PI deficiency, for example, have increased risk of suffering from severe early-onset emphysema, the result of unregulated destruction of lung tissue by human leukocyte elastase. The administration of exogenous human a1PI has been shown to inhibit elastase and is associated with improved survival and reduction in the rate of decline of lung function in a1PI-deficient patients (Crystal et al., Ain. J. Respir. Crit. Care Med. 158: 49-59 (1998); R. Mahadeva and D. Lomas, Thorax 53: 501-505 (1998) for a review.)

Because of its therapeutic utility, commercial a1PI production has been the subject of considerable research. Much progress has been made in the production of recombinant AAT in *E. coli* (R. Bischoff et al., Biochemistry 30: 3464-3472 (1991)), yeast (K. Kwon et al., J. Biotechnology 42: 191-195 (1995); Bollen et al., U.S. Pat. No. 4,629,567), and plants (J. Huang et al., Biotechnol. Prog. 17: 126-33 (2001)), and by secretion in the milk of transgenic mammals (G. Wright et al., Biotechnology, 9: 830-834 (1991); A. L. Archibald, Proc. Natl. Acad. Sci. USA, 87: 5178-5182 (1990)).

However, isolation of a1PI from human plasma is presently the most efficient practical method of obtaining a1PI in quantity, and human plasma is the only FDA-approved source.

A number of processes for isolating and purifying a1PI from human plasma fractions have been described, involving combinations of precipitation, adsorption, extraction, and chromatographic steps.

Most published processes for a1PI isolation begin with one or more fractions of human plasma known as the Cohn fraction IV precipitates, e. g. Cohn fraction IV-1 or fraction IV1-4, which are obtained from plasma as a paste after a series of ethanol precipitations and pH adjustments (E. J. Cohn et al., J. Amer. Chem. Soc., 68: 459-475 (1946)).

M. H. Coan et al., Vox Sang., 48 (6): 333-342 (1985) describe a method in which a1PI was purified from frozen Cohn fraction IV-1 paste by polyethylene glycol precipitation and DEAE-Sepharose chromatography. R. H. Hein et al., Eur. Respir. J. Suppl., 9: 16s-20s (1990) also used Cohn IV-1 paste as starting material for commercial production of a1PI in a similar process as disclosed in Coan et al.

WO 95/35306 discloses a method starting from Cohn fraction $IV_1+IV_4$-precipitate obtained as described therein, which is subjected to a polyethylene glycol/$ZnCl_2$-precipitation. Said precipitation is followed by another $ZnCl_2$-precipitation before the re-solubilized precipitate is applied to a QAE-column.

WO 98/00154 teaches a process wherein a washing step has been included subsequently to Cohn-fractionation and before subjecting the a1PI-comprising material to further processing steps. In this method the $IV_1+IV_4$-paste is suspended in water or saline solution. Soluble proteins including albumin, globulins such as alpha-1-globulin and beta-globulin are then separated from the insoluble proteins comprising a1PI by filtration, centrifugation or the like. The residue is washed with water or saline solution to remove additional soluble protein physically trapped in the insoluble paste. Similar as described in WO 95/35306, the material is then subjected to PEG- and ZnCl2-precipitations and applied to an ion-exchange chromatography step.

As mentioned above, several other processes for a1PI from human plasma fractions have been described in the art.

However, while a1PI is an effective treatment for emphysema due to alpha-1-antitrypsin deficiency, treatment is very costly (currently about $25,000 per year), due to the limited supply and a complex manufacturing process. There remains a need for more efficient and cost-effective methods for isolating human a1PI from plasma. The present invention addresses this need.

SUMMARY OF THE INVENTION

The invention is directed to an improved method for the purification of alpha-1 proteinase inhibitor (a1PI) from protein fractions, wherein the yield of a1PI can be increased by thawing and incubating the protein fraction at an ambient temperature of 2-25° C. The method for the purification of alpha-1 proteinase inhibitor (a1PI) from protein fractions comprises the steps of providing a frozen protein fraction comprising a1PI, thawing it at an ambient temperature of 2-25° C. until the protein fraction has reached ambient temperature, and incubating the thawed protein fraction for at least 15 h at an ambient temperature of 2-25° C. before subjecting it to a washing step. According to the method of the present invention the yield of a1-PI can be increased significantly due to a reduction of a1PI loss during the subsequent washing step.

DETAILED DESCRIPTION OF THE INVENTION

Figure 1:
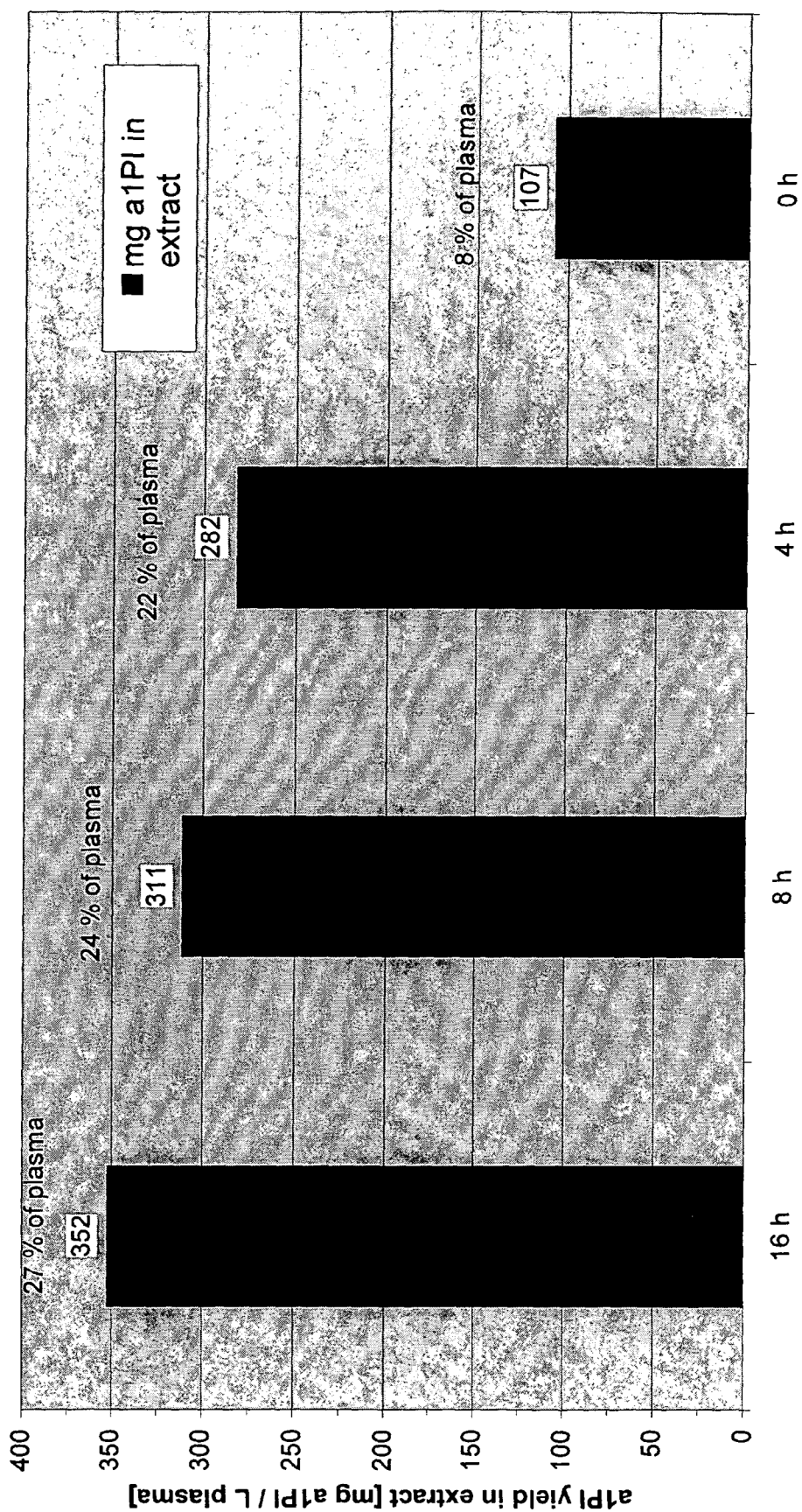
FIG. 1: a1PI yield (mg a1PI/liter plasma) in the extract of IV-1 paste obtained by using filtration as separation method and after washing at pH 6.0: influence of thawing time at 4° C.

The invention relates to a method for the purification of alpha-1 proteinase inhibitor (a1PI) from a protein fraction comprising the steps of providing a frozen protein fraction comprising a1PI, thawing it at an ambient temperature of 2-25° C. until the protein fraction has reached ambient temperature, incubating said thawed protein fraction for at least 15 h at an ambient temperature of 2-25° C., and subjecting it to a washing step.

The protein fractions can be derived from various sources. Useful sources include plasma, a1PI produced by recombinant methods, or any other source comprising a1PI.

There are many methods known in the art for precipitating proteins from solution, such as by the addition of salts, alcohols, and polyethylene glycol, often in combination with cooling and various pH adjustments. The separation of the precipitate from the solution may be accomplished by centrifugation, filtration or the like. If filtration is used as separation method, a filter aid may be used. One useful filter aid is CELPURE, which comprises 96-98% $SiO_2$ The present invention will be applicable to most a1PI-comprising protein precipitates containing recoverable a1PI activity. The term "protein fraction" as used herein refers to a1PI-comprising protein precipitate prepared by one or more of these known methods.

Protein fractions useful for the present invention include ethanol-precipitated plasma fractions such as, for example, Cohn fraction IV, such as Cohn fraction $IV_1$, and/or Cohn fraction $IV_4$, Cohn fraction $IV_1+IV_4$, and Cohn fraction IV-1, 4. The protein fraction can further comprise a composition of more than one plasma fraction.

In an embodiment of the present invention, the protein fraction is of human origin.

Protein fractions may be stored frozen at ambient temperatures of >−20° C., for example at 4-8° C. until further processing. According to an embodiment of the present invention, the frozen protein fractions include portions of about 0.05 kg of Cohn paste in the form of a block with a size of about 4×4×3 $cm^3$; portions of about 0.6 kg of Cohn paste in the form of a block with a size of about 8×8×9 $cm^3$. The protein fraction may also be stored in 10 liter plastic containers with a size of about 32×21×15 $cm^3$.

According to an embodiment of the present invention, the frozen protein fraction is thawed at an ambient temperature of 2-25° C. until the protein fraction has reached ambient temperature.

As used herein, the term "thawed" protein fraction relates to a protein fraction which has reached ambient temperature. Accordingly, the term "thawing" relates to the process of incubating the frozen protein fraction at an ambient temperature above the freezing temperature until the entire protein fraction has reached said ambient temperature.

Examples of useful ambient temperatures for thawing the protein fraction includes temperatures not exceeding 15° C., not exceeding 8° C., and not exceeding 5° C. One useful ambient temperature is about 4° C.

In an embodiment of the present invention, thawing may be accelerated by crushing the frozen protein fraction.

The time period required until the protein fraction has reached ambient temperature depends on several parameters, such as the mass of the protein fraction, the form of the frozen protein fraction, the temperature in which the protein fraction has been stored before thawing, as well as the ambient temperature in which the protein fraction is thawed.

The thawing may be monitored by placing temperature sensors on the protein fraction. The sensors may be placed on the surface as well as inside of the protein fraction. The information resulting from the temperature sensors may be used to determine the time periods for thawing and incubation of the protein fraction.

In an embodiment of the present invention, the protein fraction is incubated for at least 15 h starting from that point in time when the protein fraction is thawed, i.e. has reached ambient temperature. In another embodiment of the present invention, the thawed protein fraction is incubated for 16 h to 19 h. According to a further embodiment of the invention, the incubation period may last up to 52 h.

Subsequently, the protein fraction is subjected to a washing step.

The term "washing step" as used herein refers to a process in which other proteins, such as albumin, globulins, and/or other impurities are removed. The washing step according to the present invention includes suspension of the protein fraction in water or saline solution. The water used for the washing step may be purified water, such as water for injection (WFI). The saline solution may be, for example, a NaCl solution from about 0.05 to about 0.15 M. The amount of water or saline solution may be 5±2 parts per part of protein fraction.

According to an embodiment of the present invention, the washing step is carried out at a temperature of less than about 15° C. and for a duration of at least about 1 h.

According to one embodiment of the present invention, the pH of the washing suspension is subsequently adjusted to about 5.5±0.2. According to another embodiment of the present invention, the pH of the washing suspension is subsequently adjusted to about 6.0±0.2.

It could be shown that a1PI loss during the washing step could be reduced by adjusting the pH to a lower level following suspension in water. By thawing and incubating the frozen paste before subjecting it to the washing step, it is not necessary to lower the pH level of the washing step, as the a1PI loss can be reduced.

According to one embodiment of the present invention, the soluble proteins, including albumin, alpha-2-globulin and beta-globulin, are then separated from the insoluble proteins, including alpha-1-proteinase inhibitor by filter press, centrifugation or the like.

In one embodiment of the present invention, a filter aid may be added. One useful filter aid is a high purity, high-performance diatomite filter aid comprising 96-98% $SiO_2$ such as CELPURE.

In a further embodiment of the present invention, the washing step as described above may be conducted several times to remove additional soluble protein physically trapped in the insoluble residue. According to one embodiment of the present invention the protein fraction is washed twice.

If a filter aid is added, it may be added at the end of the first washing step before start of filtration.

According to an embodiment of the present invention, the washed protein fraction is subjected to subsequent purification steps until a final pharmaceutical preparation.

The subsequent purification steps used according to one embodiment of the present invention is a polyethylene-glycol (PEG) precipitation, followed by a $ZnCl_2$-precipitation, a viral inactivation by a solvent-detergent treatment, an anion-exchange chromatography, and a post-treatment of the a1PI-comprising eluate.

The PEG precipitation may be carried out by resuspending the insoluble protein residue in about 5±2 volumes of water at pH of 8.5±0.5 per volume of residue at a temperature of about 15° C.±5° C. for preferably about 6 hours, although shorter or longer times may be used. Solid Tris is then added to a final concentration of 10±5 mM and solid NaCl is added to a final concentration of 150±20 mM and the pH is adjusted to 8.0. Polyethylene glycol 3350 is then added to a final concentration of 15±5.% wt/wt and is mixed at about 15±5° C. for about 1 hour to precipitate alpha-2-globulin.

The PEG precipitate which forms is removed by a filter press. The filter press is washed before and after filtering with a solution containing 150±25 mM NaCl and 15±5% wt/wt PEG at a pH 8.0±0.5. Alternatively, the precipitate may be removed by centrifugation.

The $ZnCl_2$ precipitation may be conducted by adding $ZnCl_2$ (100±10 mM) to the PEG supernatant to a final concentration of 6±5 mM and the solution is adjusted to pH 7.5±0.5. The solution is cooled to about 5±5° C. and mixed for at least about 1 hour. The $ZnCl_2$ precipitates crude a1PI. The crude a1PI is concentrated by filtration, for example, by Prostak™ filtration, as described in "Prostak Open-Channel Modules" by Millipore Corporation, which is incorporated herein by reference, or by centrifugation and the filtrate is removed. The concentrated suspension or precipitate may be frozen for future processing.

For viral inactivation, the crude alpha-1-PI is reed in about 50 mM NaEDTA through Prostak by recirculating. A sugar, for example, sucrose, in an amount of about 15±5% wt/wt (or about 0.25±0.05 M $Na_3$citrate) is added as a stabilizer during viral inactivation. The solution is mixed at 15±5° C. until the sucrose is dissolved.

The a1PI-comprising solution is virus inactivated by solvent-detergent (SD) treatment. A solution of 10±1% wt/v polysorbital 80 and 3±0.3% wt/wt tri-n-butyl phosphate is added to the a1PI solution to a final concentration of 1.0±0.5% wt/v polysorbate 80 and 0.3±0.15% wt/wt tri-n-butyl phosphate. The solution is then incubated at 27±3° C., pH 8±0.5 for not less than 6 hours to inactivate any viruses which may be present in the a1PI.

It has been found that the presence of sugar, e.g., sucrose, as a stabilizer during viral inactivation by solvent-detergent treatment increases the yield of a1PI in units as compared to a control, i.e., a1PI solution viral inactivated by solvent detergent without sugar as a stabilizer. The increase in yield may be at least 10%, at least 20% or at least 30%.

After said incubation, the treated a1PI solution is cooled to 0-10° C. and the pH is adjusted to 8.0±0.1.

Anion-exchange chromatography is carried out by diluting the SD treated solution with about 1 volume of water per volume of SD treated solution. The diluted solution is then applied to a pre-equilibrated QAE chromatography medium or other similar anion-exchange medium which binds a1PI allowing other proteins to be separated from the a1PI. Either batch or column chromatography may be used. After a1PI has been absorbed onto the medium, it is washed with a buffer comprising 20±10 mM NaCl and 20±10+mM sodium phosphate ($NaH_2PO_4$) at a pH of 8±1 to remove unbound material, including beta-proteins. a1PI is then eluted from the anion-exchange chromatography medium with an elution wash comprising 100±50 mM NaCl and 20±10 mM sodium phosphate, at a pH of 8±1. The eluate which includes a1PI is collected for further processing.

After the removal of a1PI, the anion-exchange medium is cleaned by washing with, in sequence: an aqueous solution comprising 2±0.2M NaCl, 20±10 mM sodium phosphate, pH 8±1; then water for injection (WFI); then an aqueous solution comprising 500 mM NaOH; and finally WFI. The chromatography medium is then stored in 2±0.2M NaCl, 20±10 mM sodium phosphate, pH 8±1.

Post-treatment of a1PI-Comprising eluate is conducted by combining the a1PI-comprising eluates and treating them with 0.1 to 1.0% wt/wt bentonite for about an hour or more to reduce the amount of apolipo-protein, for example, to less than about 0.01 mg/ml apolipo-protein A and less than about 0.01 mg/ml apolipo protein B. The bentonite is removed by filtration, preferably by Cuno® filtration, for example, as described in "Zeta Plus® C Series Filter Medium" by Cuno Inc. which is incorporated herein by reference. The resulting solution is concentrated by ultrafiltration until the a1PI activity is at least 21.5 mg active a1PI/ml. The concentrated product is then filtered through a 0.45 micron filter to remove any particulate matter. The a1PI is then Planova 15N filtered to remove virus, sterile filtered through a 0.22 micron filter to be dispensed into vials and lyophilized for storage. A1PI is stored at 2-8° C.

The lyophilized a1PI may be re-dissolved in sterile water for administration to patients.

a1PI activity of the reconstituted a1PI may be determined by a chromogenic assay. Such an assay utilizes a trypsin sensitive chromogenic substrate which releases p-nitroaniline in the presence of trypsin (supplied by Sigma Chemical Co. of St Louis, Mo.). The p-nitroaniline released is detected at 405 nm. a1PI inhibits the release of p-nitroaniline from the substrate. The activity of a1PI in the product is determined by reference to a standard a1PI activity curve. Chromogenic assay of reconstituted lyophilized a1PI prepared according to the above process shows a specific activity of at least about 1.0 unit/OD280. In one embodiment of the present invention, the a1PI activity is determined by measuring the inhibition of porcine pancreas elastase (Boehringer Mannheim) using succinyl-(alanine)$_3$-para-nitroanilide (Bachem Fine Chemicals) as substrate as described in E. H. Mattes et al., Vox Sang., 81: 29-36 (2001).

The total protein content can be determined with Coomassie Blue according to Bradford.

According to an embodiment of the present invention, the final pharmaceutical preparation may be infused into a patient at a rate of about 0.08 ml/kg body weight per minute for the first 10 minutes. If the patient does not experience any discomfort, the rate may be increased as tolerated. If tolerated, subsequent infusions to the same patient may be at the higher rate. If adverse events occur, the rate should be reduced or the infusion interrupted until the symptoms subside. The infusion may then be resumed at a rate which is tolerated by the patient.

If large doses are to be administered, several reconstituted vials of a1PI may be pooled in an empty, sterile I.V. infusion container using aseptic technique.

EXAMPLES

Example 1

100 g aliquots of IV-1 paste obtained by Cohn fractionation using filtration as separation method and by using CELPURE as filter aid were thawed for 16, 8, 4 or 0 hours at 4° C. and then washed in parallel with 249.1 ml of WFI at 5-7° C., stirred for 10 min., adjusted to pH 6.0 with 1 M NaOH and stirred for another 10 min. After centrifugation at 5000 rpm at 4° C. for 15 min samples of the supernatant were drawn and the remaining paste including CELPURE was extracted with the 5.5 fold volume of WFI at 17.5° C., stirred for 30 min, adjusted to pH 8.8 and stirred for another 15.5 h at 17.5° C. with pH adjustments after 1, 2, 3, 5, 7 and 8 hours (after first pH adjustment to pH 8.8). After a further centrifugation at 5000 rpm at 4° C. for 15 min, the supernatant was decanted and samples were drawn.

FIG. 1 shows an increase in a1PI yield in the extract with increasing incubation duration. Without thawing and incubating the frozen paste, 8% of the plasma a1PI could be recovered in the extract, whereas after 4 h of incubation at an ambient temperature of 4° C., the yield increased to 22% of plasma a1PI, after 8 h incubation to 24% and after 16 h to 27%. The a1PI content of the extract increased from 107 mg/L plasma without incubation to 282 mg/L plasma after 4 h incubation, to 311 mg/L plasma after 8 h and to 352 mg/L plasma after 16 h incubation at ambient temperature.

Figure 2:
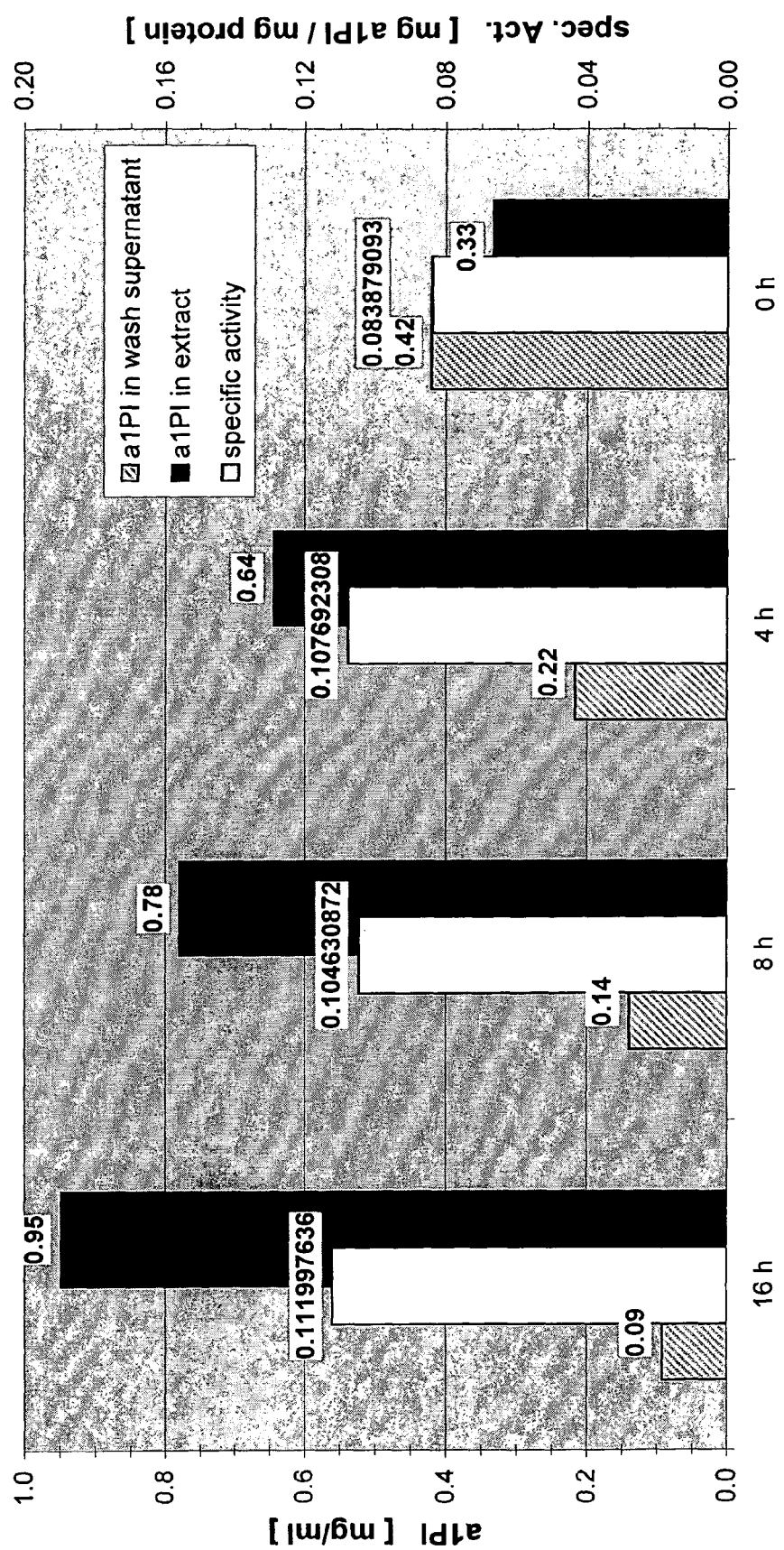
FIG. 2: a1PI yield (mg/ml) in the extract compared to the a1PI content of the wash supernatant (mg/ml) and the specific activity of the extract (mg a1PI/mg protein) of IV-1 paste obtained by using filtration as separation method and after washing at pH 6.0: influence of thawing time at 4° C.

FIG. 2 depicts the increase in total a1PI content of the extract from 0.33 to 0.95 mg/ml with increasing incubation time. Correspondingly, the total a1PI content in the wash supernatant decreased from 0.42 to 0.09 mg/ml. The specific activity of the extract increased slightly from 0.084 to 0.112 mg a1PI per mg total protein.

Example 2

50 g aliquots of IV-1 paste obtained by Cohn fractionation using centrifugation as separation method were thawed for 16, 8, 4 or 0 hours at 4° C. and then washed in parallel with 350 ml of WFI at 5-7° C. stirred for 10 min, adjusted to pH 5.5 or pH 6.0 with 1 M NaOH and stirred for another 10 min. After addition of 21.2 g of CELPURE and stirring for further 10 min, centrifugation at 5000 rpm at 4° C. for 15 min was started. Samples of the supernatant were drawn and the remaining paste including CELPURE was extracted with the 5.5 fold volume of WFI at 17.5° C. with pH adjustments after 1, 2, 3, 5, 7 and 8 hours (after first pH adjustment to pH 8.8). After a further centrifugation at 5.000 rpm at 4° C. for 15 min, the supernatant was decanted and samples were drawn.

Figure 3:
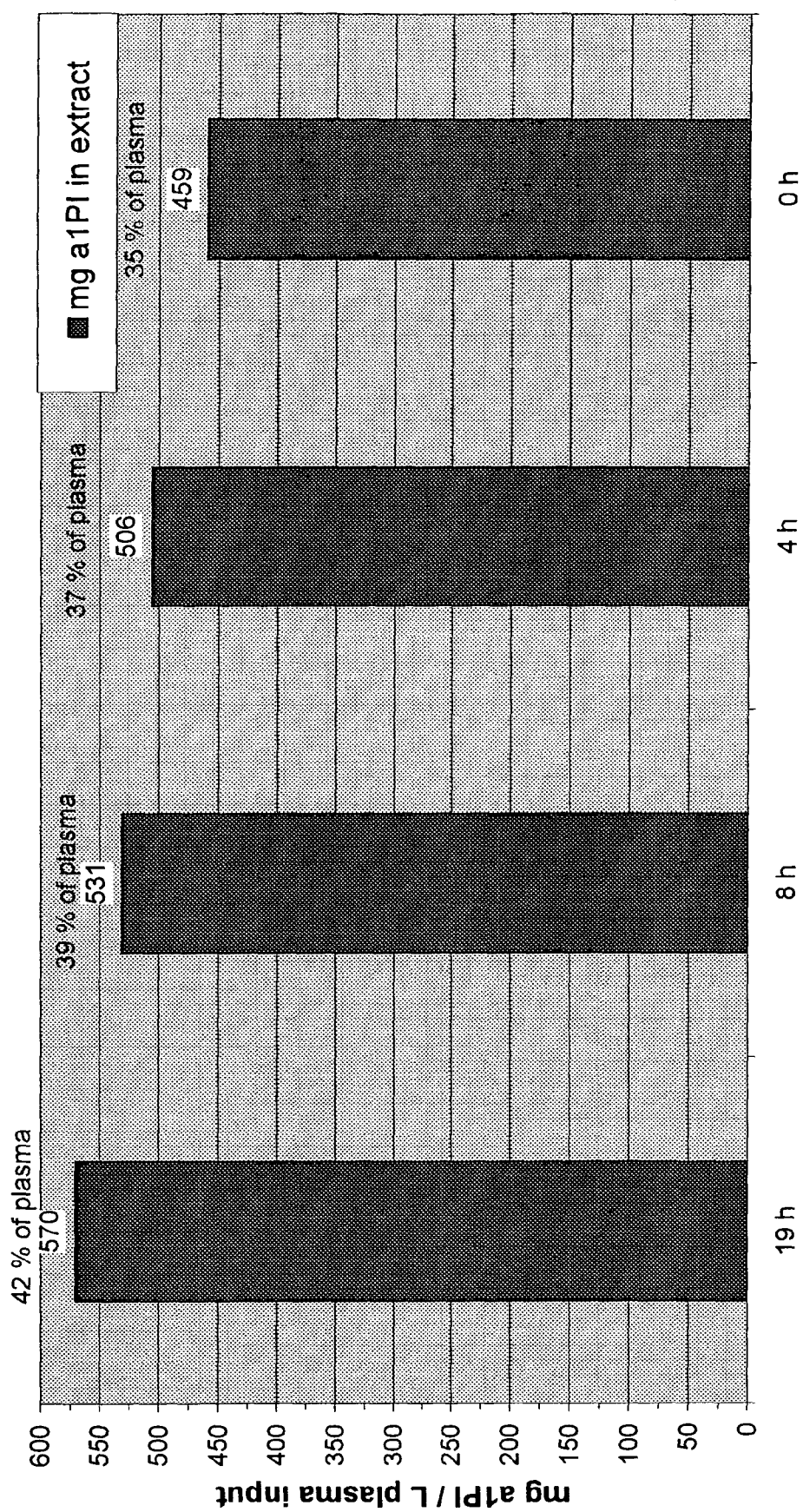
FIG. 3: a1PI yield (mg a1PI/liter plasma) in the extract of IV-1 paste obtained by using centrifugation as separation method and after washing at pH 5.5: influence of thawing time at 4° C.

FIG. 3 shows an increase in a1PI yield in the extract with increasing incubation duration followed by a washing step at pH 5.5. Without thawing and incubating the frozen paste, 35% of the plasma a1PI could be recovered in the extract, whereas after several hours of incubation at an ambient temperature of 4° C. the yield increased to up to 42% of plasma a1PI after 19 h incubation. The a1PI content of the extract increased from 459 mg/L plasma without incubation to 506 mg/L plasma after 4 h incubation, to 531 mg/L plasma after 8 h and to 570 mg/L plasma after 19 h incubation at ambient temperature.

Figure 4:
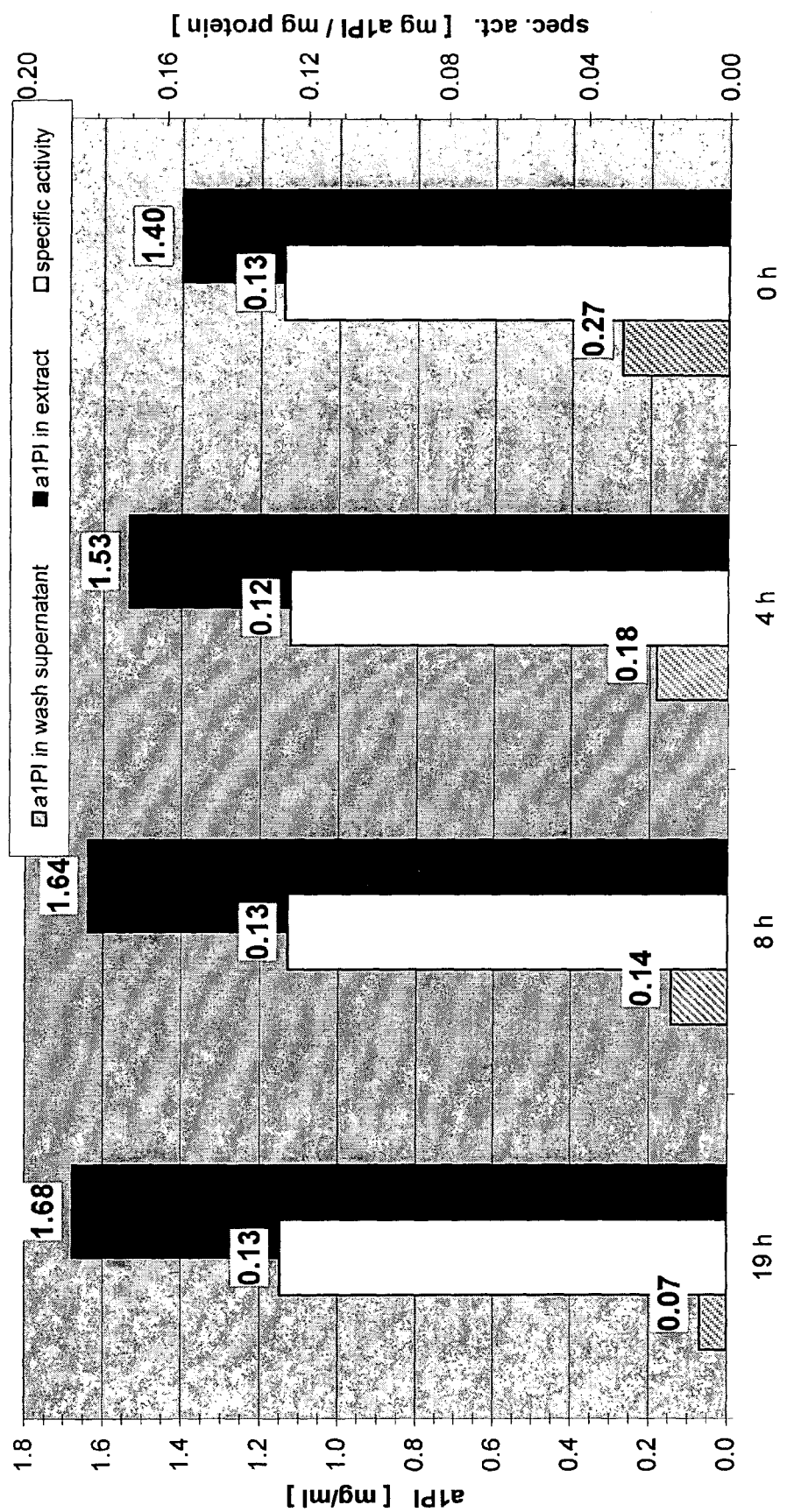
FIG. 4: a1PI yield (mg/ml) in the extract compared to the a1PI content of the wash supernatant (mg/ml) and the specific activity of the extract (mg a1PI/mg protein) of IV-1 paste obtained by using centrifugation as separation method and after washing at pH 5.5: influence of thawing time at 4° C.

FIG. 4 depicts the increase in total a1PI content of the extract from 1.42 to 1.68 mg/ml with increasing incubation time. Correspondingly, the total a1PI content in the wash supernatant decreased from 0.27 to 0.07 mg/ml. The specific activity of the extract was not significantly affected.

Figure 5:
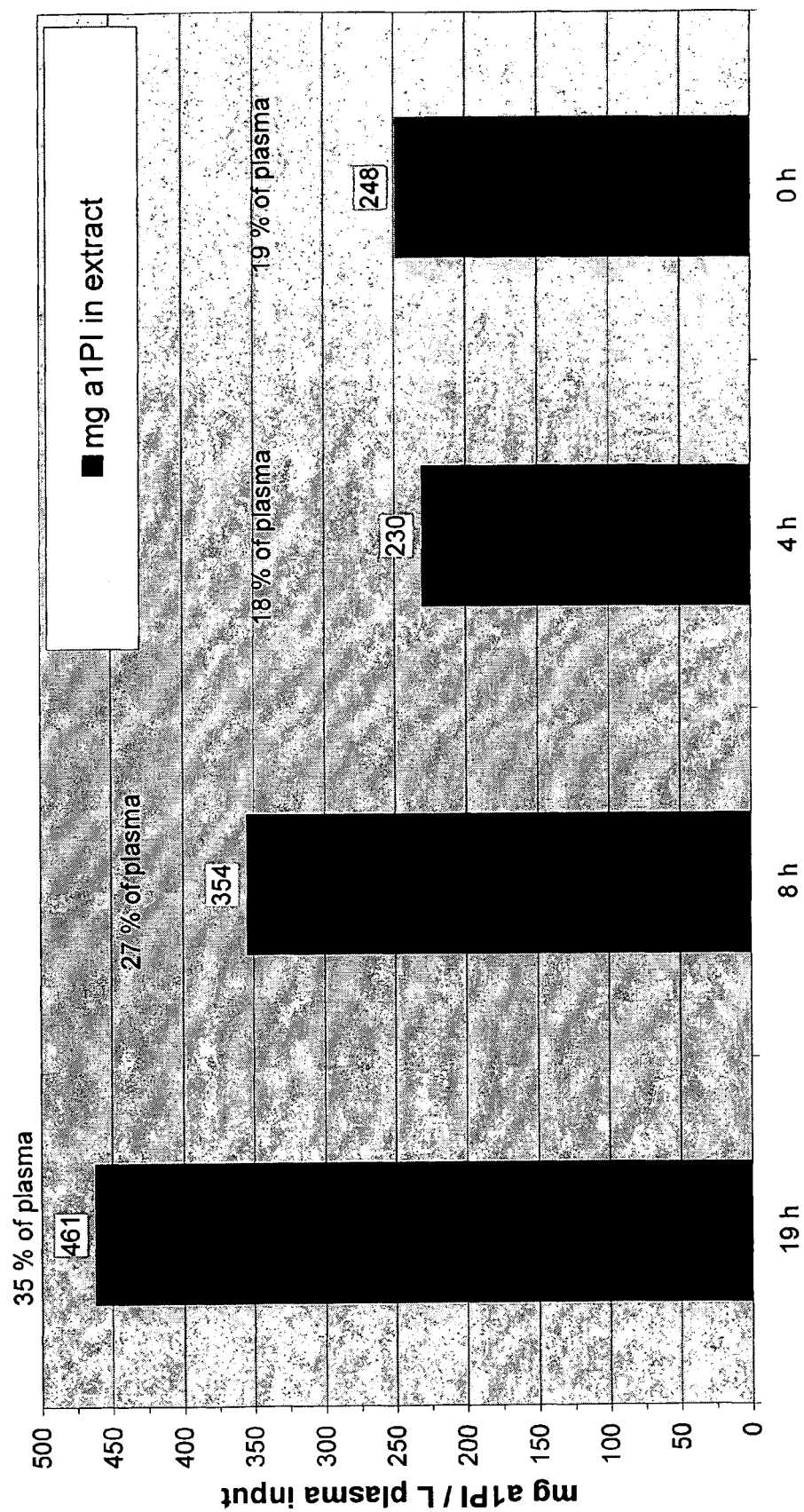
FIG. 5: a1PI yield (mg a1PI/liter plasma) in the extract of IV-1 paste obtained by using centrifugation as separation method and after washing at pH 6.0: influence of thawing time at 4° C.

FIG. 5 reveals also an increase in a1PI yield in the extract with increasing incubation duration, even followed by a wash step at pH 6.0. The yield increased from 19% of plasma to 35% of plasma a1PI after 19 h of incubation. The a1PI content of the extract increased from 248 mg/L plasma without incubation to 461 mg/L plasma after 19 h of incubation at ambient temperature.

Figure 6:
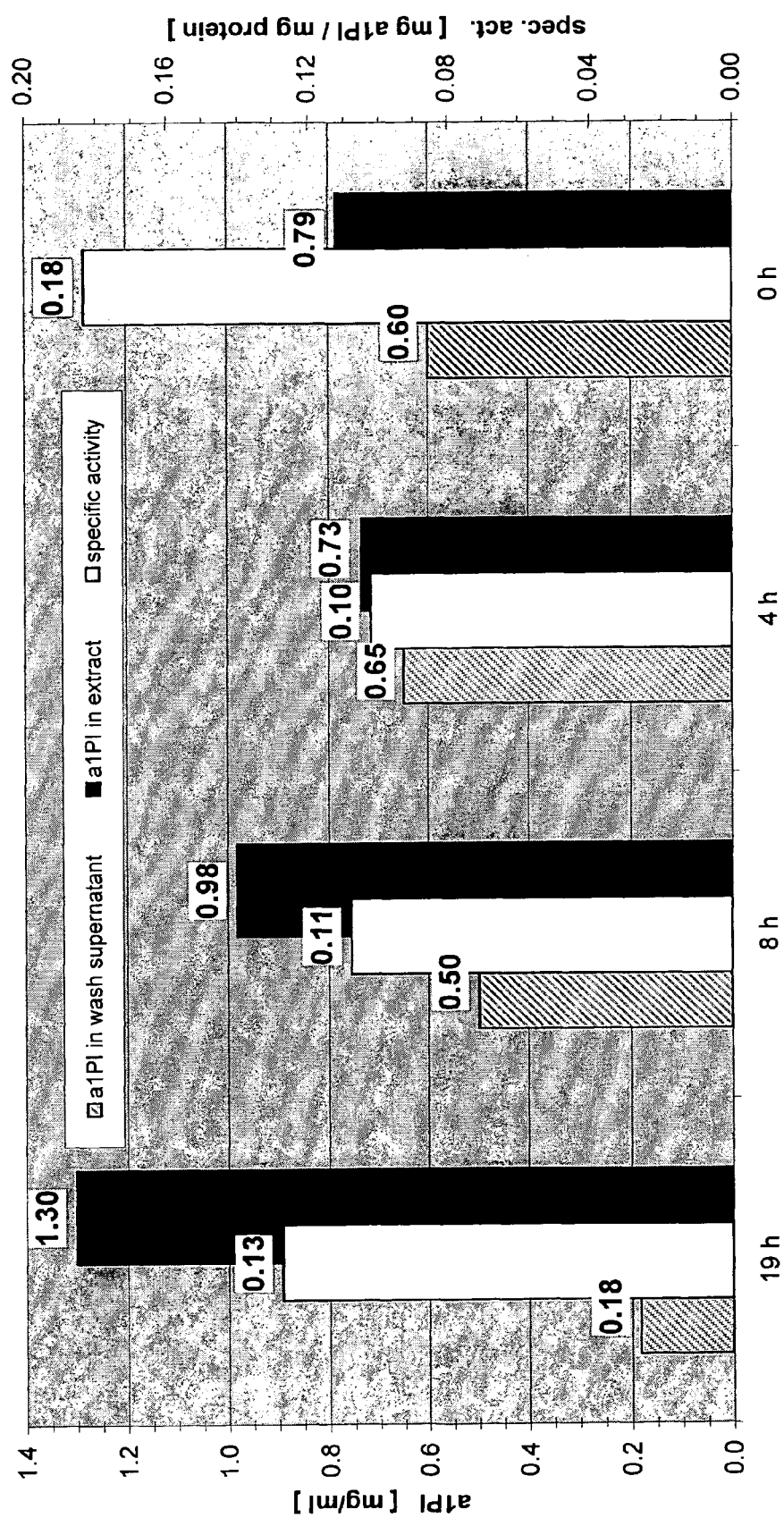
FIG. 6: a1PI yield (mg/ml) in the extract compared to the a1PI content of the wash supernatant (mg/ml) and the specific activity of the extract (mg a1PI/mg protein) of IV-1 paste obtained by using centrifugation as separation method and after washing at pH 6.0: influence of thawing time at 4° C.

FIG. 6 shows the increase in total a1PI content of the extract from 0.79 to 1.30 mg/ml with increasing incubation time. Correspondingly, the total a1PI content in the wash supernatant decreased from 0.60 to 0.18 mg/ml. The specific activity of the extract varied slightly from 0.10 to 0.18 mg a1PI per mg total protein.

Example 3

The same procedure as described in Example 2 has been conducted using 600 g aliquots of IV-1 paste and with the modification of using filtration instead of centrifugation for the separation of the pre-washed paste.

Figure 7:
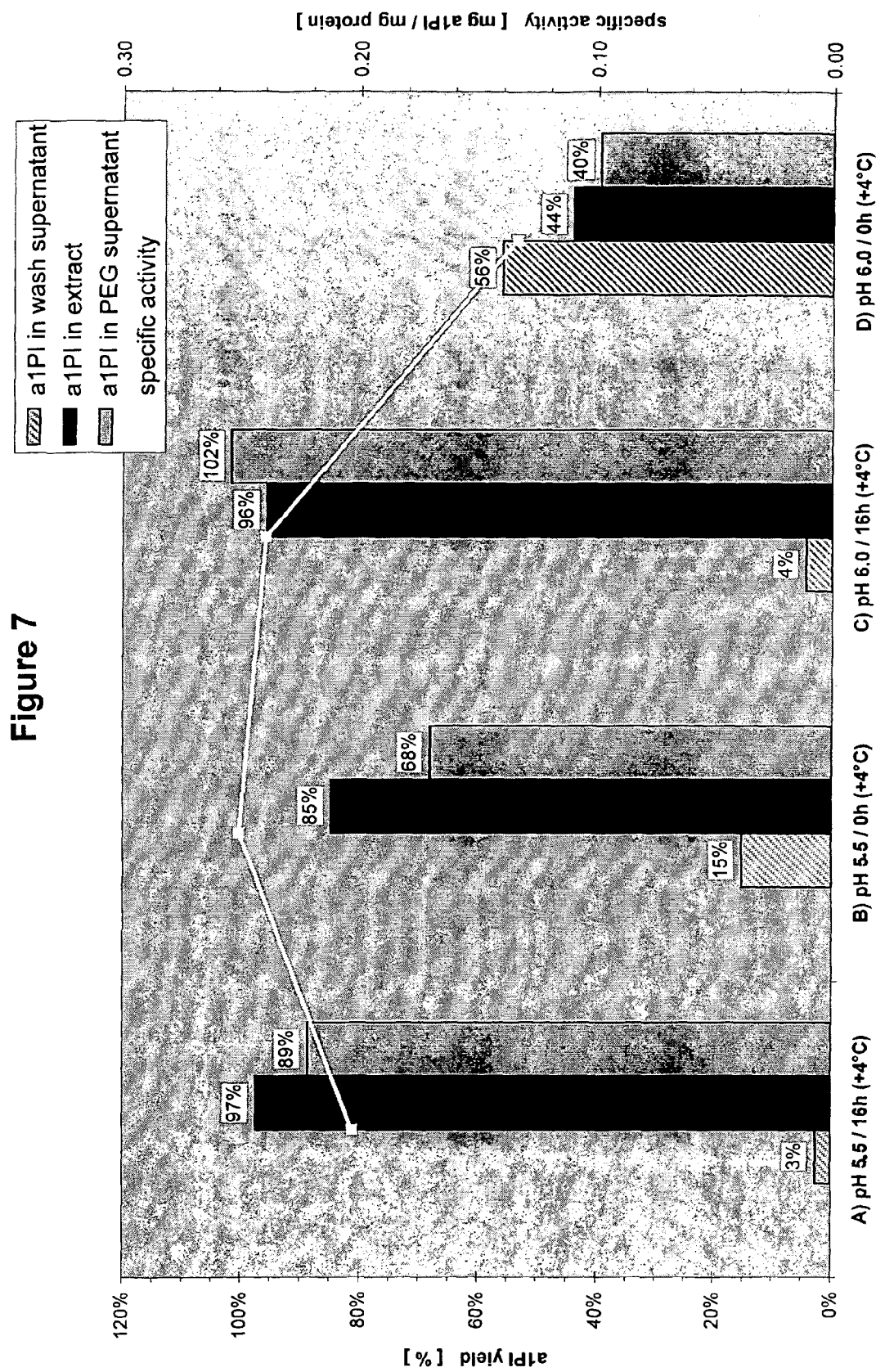
FIG. 7: a1PI yield (% of total paste) in the extract compared to the a1PI content of the wash supernatant, the a1PI content of the PEG supernatant and the specific activity of the PEG supernatant (mg a1PI/mg protein) of IV-1 paste obtained by using centrifugation as separation method: influence of thawing time at 4° C. and pH of the washing step

FIG. 7 compares the relative a1PI yield increase [in % of total paste] after 16 h of incubation followed by a washing step at pH 5.5 (left hand part) with the a1PI yield increase after the same incubation period followed by a washing step at pH 6.0 (right hand part). Whereas the yield without incubation and a following wash-step at pH 6.0 is significantly lower than the yield after a washing step at pH 5.5, incubation of the paste for 16 h increased the yield to similar values due to a drastic reduction of a1PI loss in the wash supernatant.

Figure 8:
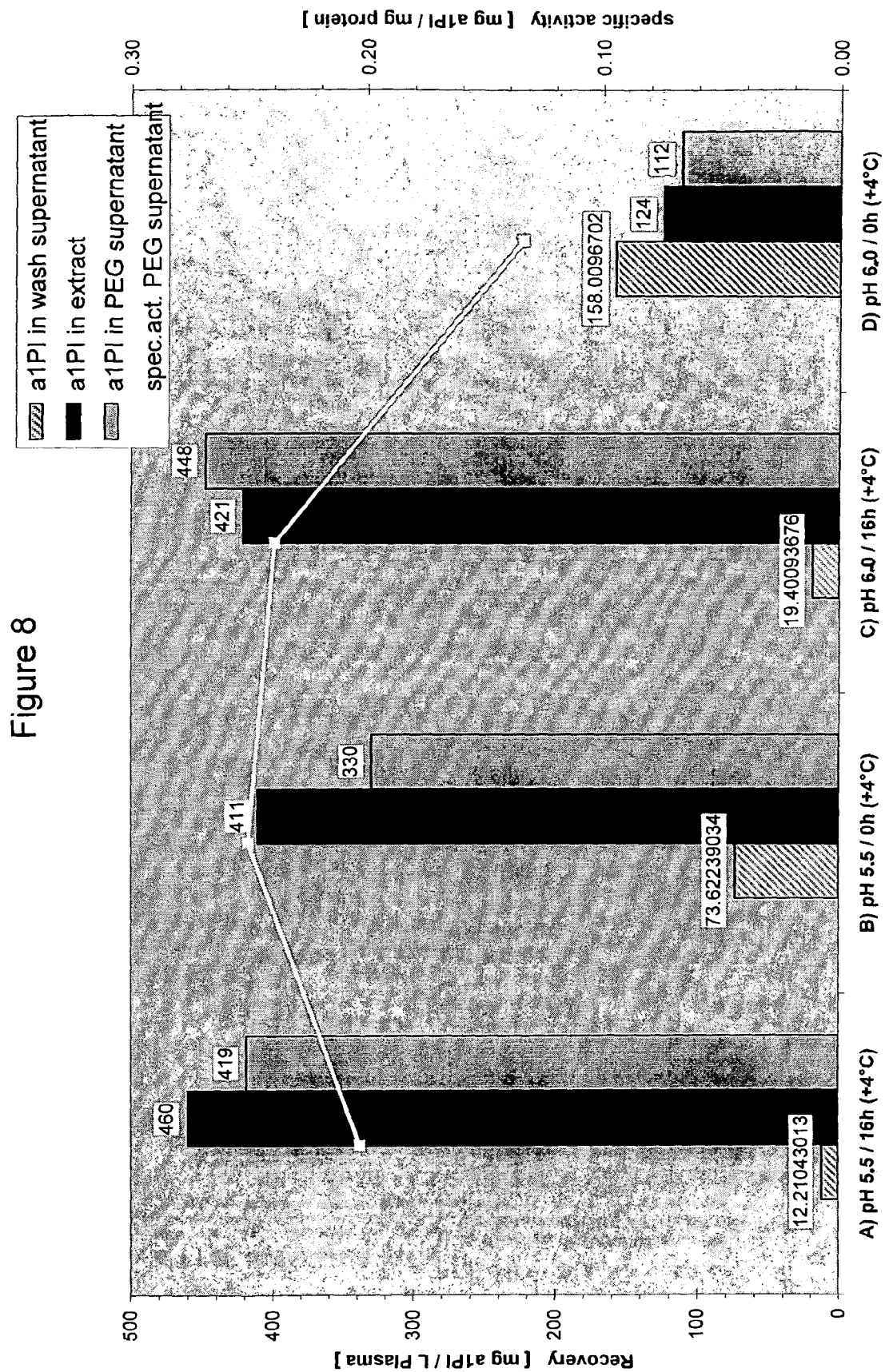
FIG. 8: Recovery of a1PI (mg a1PI/liter plasma) in the extract compared to the recovery of a1PI of the wash supernatant, the recovery of a1PI of the PEG supernatant and the specific activity of the PEG supernatant (mg a1PI/mg protein) of IV-1 paste obtained by using centrifugation as separation method: influence of thawing time at 4° C. and pH of the washing step

FIG. 8 shows said comparison for the total a1PI recovery in mg per L plasma.

Figure 9:
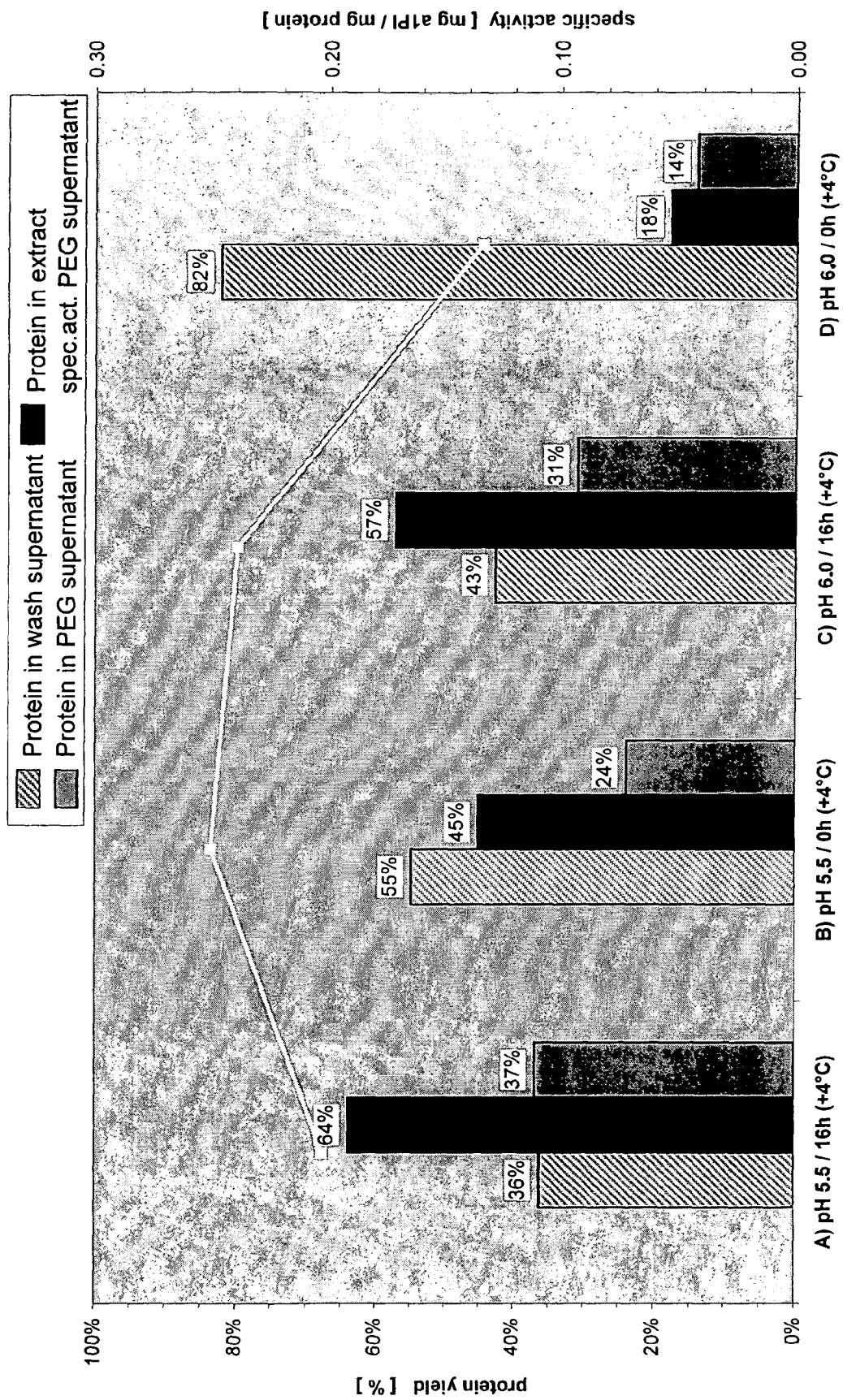
FIG. 9: Total Protein yield (% of total paste) in the extract (determined by bicinchoninic acid (BCA) assay) compared to the total protein content of the wash supernatant, the total protein content of the PEG supernatant and the specific activity of the PEG supernatant (mg a1PI/mg protein) of IV-1 paste obtained by using centrifugation as separation method: influence of thawing time at 4° C. and pH of the washing step

FIG. 9 depicts the corresponding comparative diagram for the total protein yield.

Example 4

Figure 10:
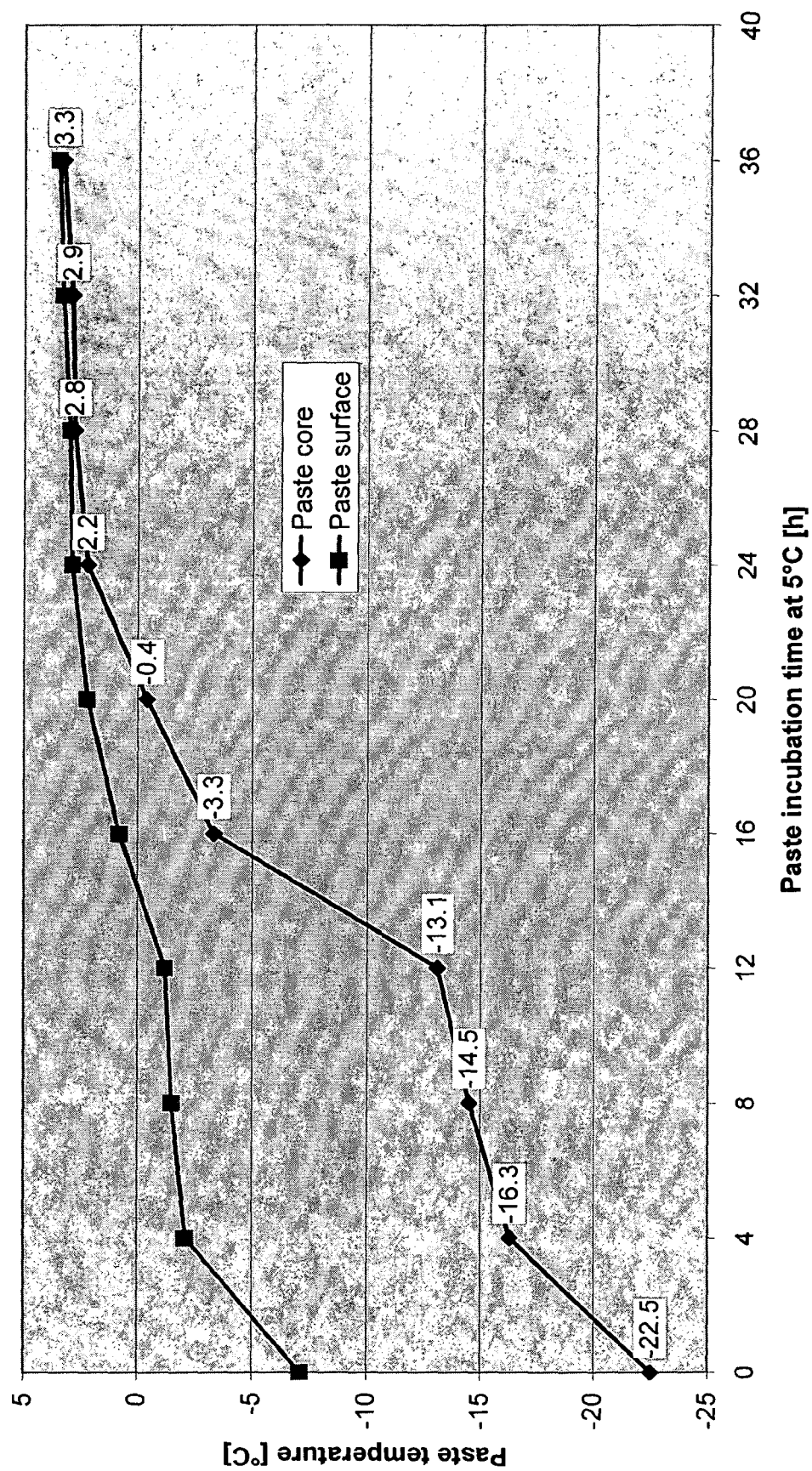
FIG. 10: Thawing curve of a frozen 10 kg block of Cohn IV-1 paste

236 kg of $IV_1$ paste (Vienna, NG pathway) obtained after centrifugation and collected in 10 kg plastic containers (32× 21×15 $cm^3$) and stored at $\leq -20°$ C. were thawed and incubated for 52 h at 5° C. After 24 h the inner core of the 10 kg container had reached ~2° C. (FIG. 10). The paste was suspended in 7 volumes of water at 5-7° C., intensively stirred for 10 min, adjusted to pH 6.0 and stirred for further 10 min at 5-7° C. After addition of CELPURE as filter aid the water washed paste was separated on a filter press containing CUNO 10-CP filter layers. The water washed paste was gained from the postwashed filter press, dissolved in 5.5 volumes of water, adjusted to pH 8.8 and stirred for 6 h at 15-20° C. Accompanying proteins were precipitated after addition of salts by 15% PEG at pH 8.0 and removed by filter press equipped with CUNO 10-CP filter layers. The filtrate containing crude extracted a1PI was precipitated by addition of 2.5 mM ZnCl2, concentrated 10 fold using a PROSTAK ultrafiltration unit and finally dissolved in 50 mM EDTA solution at pH 8.0 and 2-8° C.

a1PI yield in the ZN/EDTA concentrate could be increased by ~20% compared to routine production with frozen paste, paste crusher and washing at pH 5.5

| Step | Specific Activity with prethawing [mg a1PI/mg] | a1PI yield with prethawing [% of extract] | a1PI yield with prethawing [% of routine process]* | Specific Activity of routine process [mg a1PI/mg] |
| --- | --- | --- | --- | --- |
| Wash filtrate | 0.01 | 12 | 40 | — |
| pH 8.8 extract | 0.07 | 100 | — | 0.06 |
| Zn/EDTA | 0.26 | 76 | 121 | 0.33 |

What is claimed is:

1. A method for the purification of alpha-1 proteinase inhibitor (a1PI) from a protein precipitate, comprising the steps of
   a. providing a frozen protein precipitate comprising a1PI, wherein the frozen protein precipitate comprises at least one Cohn fraction selected from the group consisting of Cohn fraction $IV_1$, Cohn fraction $IV_4$, Cohn fraction $IV_1+IV_4$ and Cohn fraction $IV_{1,4}$,
   b. thawing the protein precipitate at an ambient temperature of 2-25° C. until the protein precipitate has reached ambient temperature, without adding a suspending solvent,
   c. maintaining the thawed protein precipitate for at least 15 h (hours) at an ambient temperature of 2-25° C., and
   d. suspending the thawed, incubated precipitate of step c in a wash solution, and washing the protein precipitate; and
   e. extracting and purifying a1PI from the thawed, washed protein precipitate of step d.

2. A method according to claim 1, wherein the Cohn fraction is obtained by using filtration as separation method and wherein the Cohn fraction comprises a filter aid.

3. A method according to claim 2, wherein the filter aid comprises 96-98% $SiO_2$.

4. A method according to claim 1, wherein the frozen protein precipitate comprising a1PI is derived from a1PI produced by recombinant methods.

5. A method according to claim 1, wherein the frozen protein precipitate is of human origin.

6. A method according to claim 1, wherein the frozen protein precipitate is crushed.

7. A method according to claim 1, wherein the frozen protein precipitate is thawed at an ambient temperature of about 4° C.

8. A method according to claim 1, wherein the thawed protein precipitate is incubated at an ambient temperature of about 4° C.

9. A method according to claim 1, wherein the thawed protein precipitate is incubated for 15 h.

10. A method according to claim 1, wherein the thawed protein precipitate is incubated for 16 h to 19 h.

11. A method according to claim 1, wherein the suspending and washing step d comprises suspending the thawed and incubated protein precipitate in water or saline solution at a temperature of less than about 15° C. for at least 1 h, subsequently adjusting the pH of the washing suspension to about 5.5 or 6.0, and separating the soluble proteins from the insoluble proteins by filtration or centrifugation.

12. A method according to claim 11, wherein the soluble proteins are separated from the insoluble proteins by filtration and a filter aid is used for said separation.

13. A method according to claim 12, wherein the filter aid comprises 96-98% $SiO_2$.

14. A method according to claim 1, wherein the washing step is conducted at least twice.

* * * * *